US010926071B2

(12) United States Patent
Brucker

(10) Patent No.: US 10,926,071 B2
(45) Date of Patent: Feb. 23, 2021

(54) METHODS FOR TREATING NAIL INFECTIONS

(71) Applicant: Jane Brucker, Sherman Oaks, CA (US)

(72) Inventor: Jane Brucker, Sherman Oaks, CA (US)

(73) Assignee: Jane Brucker, Los Gatos, CA (US)

( * ) Notice: Subject to any disclaimer, the term of this patent is extended or adjusted under 35 U.S.C. 154(b) by 892 days.

(21) Appl. No.: 15/603,028

(22) Filed: May 23, 2017

(65) Prior Publication Data

US 2017/0340871 A1 Nov. 30, 2017

Related U.S. Application Data

(60) Provisional application No. 62/340,862, filed on May 24, 2016.

(51) Int. Cl.

| | |
|---|---|
| ***A61M 35/00*** | (2006.01) |
| ***A61F 13/10*** | (2006.01) |
| ***A61F 13/06*** | (2006.01) |
| ***A61F 13/00*** | (2006.01) |
| ***A61K 31/496*** | (2006.01) |
| ***A61K 31/137*** | (2006.01) |

(52) U.S. Cl.

CPC ....... *A61M 35/00* (2013.01); *A61F 13/00055* (2013.01); *A61F 13/00063* (2013.01); *A61F 13/068* (2013.01); *A61F 13/105* (2013.01); *A61K 31/137* (2013.01); *A61K 31/496* (2013.01); *A61M 2205/584* (2013.01); *A61M 2210/083* (2013.01); *A61M 2210/086* (2013.01)

(58) Field of Classification Search

CPC . A61M 35/00; A61F 13/00063; A61F 13/068; A61K 31/137; A61K 31/496

See application file for complete search history.

(56) References Cited

U.S. PATENT DOCUMENTS 6,143,794 A * 11/2000 Chaudhuri ........... A61K 9/0012 514/655

FOREIGN PATENT DOCUMENTS

CN 100421732 * 10/2008

OTHER PUBLICATIONS

Nailsatpanache (Acrylic, Do It Yourself: Do-It-Yourself Acrylic Nails—Part 2: Nail Dehydrator and Primer, https://nailsatpanache.wordpress.com/2013/05/15/do-it-yourself-acrylic-part-2/, May 15, 2013, Accessed Aug. 17, 2020) (Year: 2013).*

English Translation of Susilo (CN 100421732) (Year: 2008).*

* cited by examiner

*Primary Examiner* — Ariana Zimbouski

(74) *Attorney, Agent, or Firm* — Fish & Richardson P.C.

(57) ABSTRACT

Provided herein are methods for treating nail infections, in particular fungal nail infections, comprising applying a drug delivery system comprising a desiccant such as silica gel to an external surface of the infected nail.

18 Claims, No Drawings

METHODS FOR TREATING NAIL INFECTIONS

CROSS REFERENCE TO RELATED APPLICATIONS

This application claims the benefit of U.S. Provisional Application Ser. No. 62/340,862, filed on May 24, 2016, the disclosure of which is incorporated herein by reference in its entirety.

TECHNICAL FIELD

This invention relates to methods for treating nail infections, and, more particularly, to methods for treating fungal nail infections.

BACKGROUND

Different kinds of fungi and bacteria can cause nail infections. Fungal nail infections account for nearly one-half of all nail disorders. A fungal nail infection occurs when a fungus attacks a fingernail, a toenail, or the nail bed (the skin under the nail). Infected nails often become thicker and begin to lift from the nail bed. It is not uncommon to see debris under the nails and discoloration of the affected area. To date, for relief of the actual infection, patients apply drops of various remedies, morning and night, which might take up to a year to have an effect or, alternatively, disappoint. Currently available options for treatment of fungal nail infections include oral antifungal drugs such as terbinafine and itraconazole, up to a year-long treatment with an antifungal nail polish called ciclopirox (Penlac), antifungal nail cream, and surgical nail removal.

Plastic press on nails are presently available to cover unsightly damaged nails. But they do not treat the underlying infection, they encourage the growth of more fungus, and may even exacerbate the infection.

Silica gel has been proven to be a safe and effective dehydrating agent especially for fungus. It has had a long history of being recommended for lockers and gym bags, etc. Silica gel has been used successfully and extensively for dehydration for fungus removal, but never from toe or fingernail infections

DETAILED DESCRIPTION OF THE INVENTION

The present application provides methods for treating an infected nail, the methods comprising applying a drug delivery system comprising a desiccant to an external surface of the infected nail of a patient in need thereof.

The invention discussed herein comprises:

1. forming silica gel into toenail or fingernail shape with adhesive on back
2. forming silica gel (the size of a toenail or fingernail) onto bandage tape In one general aspect of the invention, the drug delivery system is in the form of a wrap, such as a bandage, designed to be conformable to a digit, such as a finger or a toe. In some embodiments the wrap comprises desiccant at a portion of the wrap configured to be proximal to the external surface of the infected nail when wrapped around the digit. The bandage may be a sock-like or thimble-like bandage. In some embodiments the bandage is removably attached to the digit, and in some embodiments at least a portion of the internal surface of the bandage is coated with an adhesive. In some embodiments, the external surface of the bandage is coated with a water impermeable coating. The water impermeable coating may also be impregnated into the bandage. In some embodiments, the desiccant is silica gel. The desiccant may, in some embodiments, include a moisture indicator which changes color depending on the presence of moisture. In some embodiments, the wrap is configured to allow the color of the moisture indicator to be determined while the wrap is wrapped around the digit, such as by inclusion of a port or opening in the wrap. In some embodiments, the desiccant is contained in a removable package. In some embodiments the desiccant can be replaced periodically, and the desiccant may be replaced with fresh or regenerated desiccant. In some embodiments an effective amount of an anti-fungal or anti-bacterial composition may be administered to the patient prior to applying the drug delivery system. In some embodiments, the anti-fungal or anti-bacterial composition is administered to the external surface of the infected nail.

In some aspects of the invention, the drug delivery system is in the form of a press-on prosthetic nail comprising silica gel, the prosthetic nail having an area and shape approximating the area and shape of the infected nail. In some embodiments the press-on prosthetic nail has a proximal surface configured to be proximal to the external surface of the infected nail and a distal surface configured to be distal to the external surface of the infected nail. The press-on prosthetic nail may, in some embodiments, be removably attached to the infected nail. In some embodiments at least a portion of the proximal surface of the press-on prosthetic nail is coated with an adhesive effective to firmly adhere the press-on prosthetic nail to the infected nail. In some embodiments, the periphery of the proximal surface of the press-on prosthetic nail is coated with the adhesive. Some embodiments of the invention comprise a release backing in contact with the adhesive such that the release backing is peelable from the press-on prosthetic nail. In some embodiments the press-on prosthetic nail is replaced periodically. In some embodiments the distal surface of the press-on prosthetic nail is paintable with a water impermeable coating or with nail polish. In some embodiments, the silica gel comprises a color changing moisture indicator. In some embodiments the press-on prosthetic nail is configured to allow the color of the moisture indicator to be assessed while the press-on prosthetic nail is adhered to the infected nail, such as by inclusion of a port, window, or opening in the press-on prosthetic nail.

Relationship Between the Components:

The silica gel press-on nails can be worn while the subject is in bare feet or in sandals. The bandages, wraps or other drug delivery systems can be worn on toes in socks and shoes.

How the Invention Works:

Silica gel is effective in destroying fungus when kept on top of the nail. Implementations including these methods can be worn throughout the-day and also, in some embodiments, provide aesthetically pleasing cosmetic coverage of the damaged nail as well. In some embodiments, therapeutic treatment of the infected nails and surfaces takes a few weeks to show some effect, instead of many months of applying drops or creams.

How to Make the Invention:

Silica gel can be formed into the shape of toe or finger nails, the same way it is shaped into balls today. An adhesive, as is used for press-on nails today, can be applied to a back surface of the press-on nail. For bandage or wrap-type embodiments, silica gel discs can be affixed to or applied in conjunction with medical tape the way gauze is added to Band-Aids today.

The adhesive to the back of the press-on silica nail can either be processed on the product or applied separately, as glue is presently optional for press-on nails today.

Silica gel can be applied in many forms to be effective for fungal infections, including being applied as silica gel drops and creams.

How to Use the Invention:

A person "wears" the silica gel on their infected nail using either a cosmetic press-on nail (which can be painted with nail polish to match a manicure or pedicure) or applied using a medicated bandage/wrap, optionally while wearing shoes and socks, until the infection dries and grows out. The press-on nails or bandages can be changed every day, every other day, once every several days, once every week, once every several weeks, or as desired by the user. In some embodiments this process takes weeks instead of months to cause a therapeutic and/or a cosmetic improvement.

Silica gel can be used for other topical fungal infections in powder or cream form, In some embodiments a press on nail or gel bandage comprising silica will take away the ugliness during the healing process-which can be much shorter period than previous methods.

As stated above, in some embodiments the present invention more rapidly cures disfigured toe- or fingernails due to fungal infection. The present invention provides additional means for treating such infections.

In some embodiments the present invention functions to dehydrate hard to reach fungus from under the nail, while providing cosmetic coverage during the healing process.

The claimed invention differs from traditional treatments for infected nails. Although silica gel has been used previously for dehydration for fungus removal, to date silica gel has not been used for treatment of toe- or fingernail infections. Cosmetic coverage is an additional benefit during treatment.

In some embodiments the present invention provides additional benefits as compared to traditional treatments for toe- or fingernail infections which fail to effectively dry out the infection as silica gel does. As a result, patients must hide their mangled nails, instead of healing them.

Silica gel has previously been proven to be a safe and effective dehydrating agent—especially for fungus, and has a long history of being recommended for lockers and gym bags, etc. A silica press-on nail or gel bandage can hide the ugliness during the healing process, which, in some embodiments, is a much shorter period than typically seen using previous methods.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It should be appreciated by those persons having ordinary skill in the art(s) to which the present invention relates that any of the features described herein in respect of any particular embodiment of the present invention can be combined with one or more of any of the other features of any other embodiments of the present application described herein, with modifications as appropriate to ensure compatibility of the combinations. Such combinations are considered to be part of the present application.

What is claimed is:

1. A method for treating an infected nail of a patient in need thereof, the method comprising applying a drug delivery system comprising a silica gel desiccant to an external surface of the infected nail of the patient, wherein the drug delivery system is in the form of a press-on prosthetic nail comprising silica gel, the press-on prosthetic nail having an area and shape approximating the area and shape of the infected nail, and the press-on prosthetic nail further having a proximal surface configured to be proximal to the external surface of the infected nail and a distal surface configured to be distal to the external surface of the infected nail.

2. The method of claim 1 further comprising, prior to applying the drug delivery system comprising desiccant to the external surface of the infected nail of a patient in need thereof, the step of administering to the patient an effective amount of an anti-fungal or anti-bacterial composition.

3. The method of claim 2 wherein the anti-fungal composition comprises one or more compounds selected from the group consisting of polyenes, allylamines, azoles, and morpholines, or pharmaceutically acceptable salts thereof.

4. The method of claim 2 wherein the antifungal composition comprises itraconzalone or terbinafine.

5. The method of claim 2 wherein the antifungal composition is administered to the external surface of the infected nail.

6. The method of claim 1 wherein the press-on prosthetic nail is removably attached to the infected nail.

7. The method of claim 6 wherein at least a portion of the proximal surface of the press-on prosthetic nail is coated with an adhesive effective to firmly adhere the press-on prosthetic nail to the infected nail.

8. The method of claim 7 wherein the periphery of the proximal surface of the press-on prosthetic nail is coated with the adhesive.

9. The method of claim 7 wherein the adhesive adheres to the infected nail upon contact with the infected nail.

10. The method of claim 7 further comprising a release backing in contact with the adhesive, wherein the release backing is peelable from the press-on prosthetic nail.

11. The method of claim 1 wherein the distal surface of the press-on prosthetic nail is paintable.

12. The method of claim 11 wherein the distal surface of the press-on prosthetic nail is paintable with a water impermeable coating.

13. The method of claim 11 wherein the distal surface of the press-on prosthetic nail is paintable with nail polish.

14. The method of claim 6 wherein the press-on prosthetic nail is periodically replaced.

15. The method of claim 14 wherein the press-on prosthetic nail is replaced daily.

16. The method of claim 6 wherein the silica gel further comprises a color changing moisture indicator.

17. The method of claim 16 wherein the press-on prosthetic nail is configured to allow the color of the moisture indicator to be assessed while the press-on prosthetic nail is adhered to the infected nail.

18. The method of claim 17 wherein the press-on prosthetic nail further comprises a port through which the color of the moisture indicator can be assessed.

* * * * *